United States Patent
Bishop et al.

(10) Patent No.: US 10,202,320 B2
(45) Date of Patent: Feb. 12, 2019

(54) CATALYST AND METHOD FOR ITS PREPARATION

(71) Applicant: JOHNSON MATTHEY PLC, London (GB)

(72) Inventors: Peter Trenton Bishop, Oxfordshire (GB); Nicholas Andrew Carthey, Oxfordshire (GB); Peter Johnston, Royston (GB)

(73) Assignee: Johnson Matthey PLC, London (GB)

( * ) Notice: Subject to any disclaimer, the term of this patent is extended or adjusted under 35 U.S.C. 154(b) by 207 days.

(21) Appl. No.: 15/193,228

(22) Filed: Jun. 27, 2016

(65) Prior Publication Data

US 2016/0304418 A1    Oct. 20, 2016

Related U.S. Application Data

(62) Division of application No. 14/232,294, filed as application No. PCT/GB2012/051623 on Jul. 10, 2012, now Pat. No. 9,409,161.

(Continued)

(30) Foreign Application Priority Data

Jul. 11, 2011  (GB) .................................... 1111819.7

(51) Int. Cl.
*B01J 23/54*  (2006.01)
*C07C 17/08*  (2006.01)
(Continued)

(52) U.S. Cl.
CPC .............. *C07C 17/08* (2013.01); *B01J 21/18* (2013.01); *B01J 23/52* (2013.01); *B01J 23/68* (2013.01); *B01J 23/8913* (2013.01); *B01J 23/8926* (2013.01); *B01J 27/02* (2013.01); *B01J 27/055* (2013.01); *B01J 31/0231* (2013.01); *B01J 31/0271* (2013.01); *B01J 31/04* (2013.01); *B01J 31/1616* (2013.01); *B01J 31/226* (2013.01);
(Continued)

(58) Field of Classification Search
CPC ........ B01J 23/52; B01J 23/54; B01J 23/8913; B01J 23/8926
USPC .......................... 502/155, 162, 167, 330, 344
See application file for complete search history.

(56) References Cited

U.S. PATENT DOCUMENTS 2,642,361 A  6/1953  Damschroder et al.
5,254,777 A  10/1993  Strebelle et al.
(Continued)

FOREIGN PATENT DOCUMENTS

CN  102029189 A  4/2011
EP  0031530  12/1980
(Continued)

OTHER PUBLICATIONS

Notice of Reasons for Rejection dated Mar. 29, 2016; Application No. 2014-519627.
(Continued)

Primary Examiner — Patricia L. Hailey
(74) Attorney, Agent, or Firm — Baker & Hostetler LLP

(57) ABSTRACT

A catalyst including gold, or a compound thereof, and sulphur, a compound of sulphur, trichloroisocyanuric acid or a metal dichloroisocyanurate on a support, together with a process for manufacturing the catalyst and its use in a chemical process are described.

19 Claims, 1 Drawing Sheet

Related U.S. Application Data

(60) Provisional application No. 61/510,739, filed on Jul. 22, 2011.

(51) Int. Cl.

| | | |
|---|---|---|
| *B01J 21/18* | (2006.01) |
| *B01J 23/52* | (2006.01) |
| *B01J 27/02* | (2006.01) |
| *B01J 37/02* | (2006.01) |
| *B01J 31/16* | (2006.01) |
| *B01J 31/22* | (2006.01) |
| *B01J 23/68* | (2006.01) |
| *B01J 23/89* | (2006.01) |
| *B01J 37/00* | (2006.01) |
| *B01J 27/055* | (2006.01) |
| *B01J 31/04* | (2006.01) |
| *B01J 31/02* | (2006.01) |
| *B01J 31/26* | (2006.01) |
| *B01J 31/28* | (2006.01) |

(52) U.S. Cl.
CPC ........... *B01J 31/2252* (2013.01); *B01J 31/26* (2013.01); *B01J 31/28* (2013.01); *B01J 37/0009* (2013.01); *B01J 37/0203* (2013.01); *B01J 37/0207* (2013.01); *B01J 37/0209* (2013.01); *B01J 37/0213* (2013.01); *B01J 37/0236* (2013.01); *B01J 2231/32* (2013.01); *B01J 2531/11* (2013.01); *B01J 2531/12* (2013.01); *B01J 2531/13* (2013.01); *B01J 2531/14* (2013.01); *B01J 2531/15* (2013.01); *B01J 2531/16* (2013.01); *B01J 2531/18* (2013.01); *B01J 2531/22* (2013.01); *B01J 2531/23* (2013.01); *B01J 2531/24* (2013.01); *B01J 2531/25* (2013.01); *B01J 2531/37* (2013.01); *B01J 2531/39* (2013.01); *B01J 2531/845* (2013.01)

(56) References Cited

U.S. PATENT DOCUMENTS

| | | | |
|---|---|---|---|
| 6,730,757 B2 | 5/2004 | Wang et al. | |
| 2005/0276741 A1 | 12/2005 | Kuperman et al. | |
| 2006/0216223 A1* | 9/2006 | DiMascio ............. C01B 11/024 423/477 |
| 2007/0037697 A1* | 2/2007 | DiMascio ................ B01J 35/08 502/232 |
| 2007/0179310 A1 | 8/2007 | Augustine | |
| 2008/0089823 A1 | 4/2008 | Kuperman et al. | |
| 2008/0206562 A1 | 8/2008 | Stucky et al. | |
| 2009/0056348 A1 | 3/2009 | Noll et al. | |
| 2010/0076208 A1 | 3/2010 | Dhingra et al. | |
| 2016/0325254 A1* | 11/2016 | Gray .................... B01J 8/067 |
| 2018/0118643 A1* | 5/2018 | Carthey ................ C07C 17/08 |

FOREIGN PATENT DOCUMENTS

| | | | |
|---|---|---|---|
| EP | 0557674 | 9/1993 | |
| EP | 1577282 | 9/2005 | |
| EP | 1757613 | 2/2007 | |
| JP | 52136104 | 11/1977 | |
| JP | 04141236 | 5/1992 | |
| JP | 2010037176 | 2/2010 | |
| JP | 2010510048 | 4/2010 | |
| RU | 2045336 C1 | 10/1995 | |
| WO | 2008063880 | 5/2008 | |
| WO | 2008103366 | 8/2008 | |
| WO | 2009056348 | 5/2009 | |
| WO | 2010055341 | 5/2010 | |
| WO | 2011/050614 | * 5/2011 | ............. B01J 31/30 |
| WO | WO 2011/050614 | * 5/2011 | |

OTHER PUBLICATIONS

Conte et al., "Reactivation of a Carbon-supported Gold Catalyst for the Hydrochlorination of Acetylene", Catal. Lett., 2008, vol. 124, pp. 165-167.

Nkosi et al., "Hydrochlorination of Acetylene Using Gold Catalysts: A Study of Catalyst Deactivation", Journal of Catalysis, 1991, vol. 128, pp. 366-377.

Nkosi et al., "Hydrochlorination of Acetylene Using Carbon-Supported Gold Catalysts: A Study of Catalyst Reactivation", Journal of Catalysis, 1991, vol. 128, pp. 378-386.

David Thompson, "New Advances in Gold Catalysis Part I", Gold Bulletin, 1998, vol. 31, No. 4, pp. 111-118.

International Search Report dated Mar. 19, 2013 in the corresponding PCT application.

Search Report dated Nov. 14, 2011, in corresponding GB priority application.

Ornella Cavalleri et al: "Ostwald ripening of vacancy islands at thiol covered Au(111)". Surface Science. vol. 340, No. 1-2, Oct. 1, 1995, pp. 960-964. XP55035876. ISSN: 0039-6028.

Yeh et al.: "Noncovalent Interaction between Gold Nanoparticles and Multiwalled Carbon Nanotubes via an Intermediatory", Journal of Nanotechnology, HINDAWI, vol. 2009, Jan. 1, 2009, pp. 1-7, XP009162105.

A. Goguet: "Remarkable stability of ionic gold supported on sulfated lanthanum oxide", Chem. Commun., Jun. 6, 2009, pp. 4889-4891. XP002690822.

G.J. Hutchings: "Reactions of alkynes using heterogeneous and homogeneous cationic gold catalysts", Top. Catal., vol. 48, Mar. 27, 2008, pp. 55-59. XP002690823.

* cited by examiner

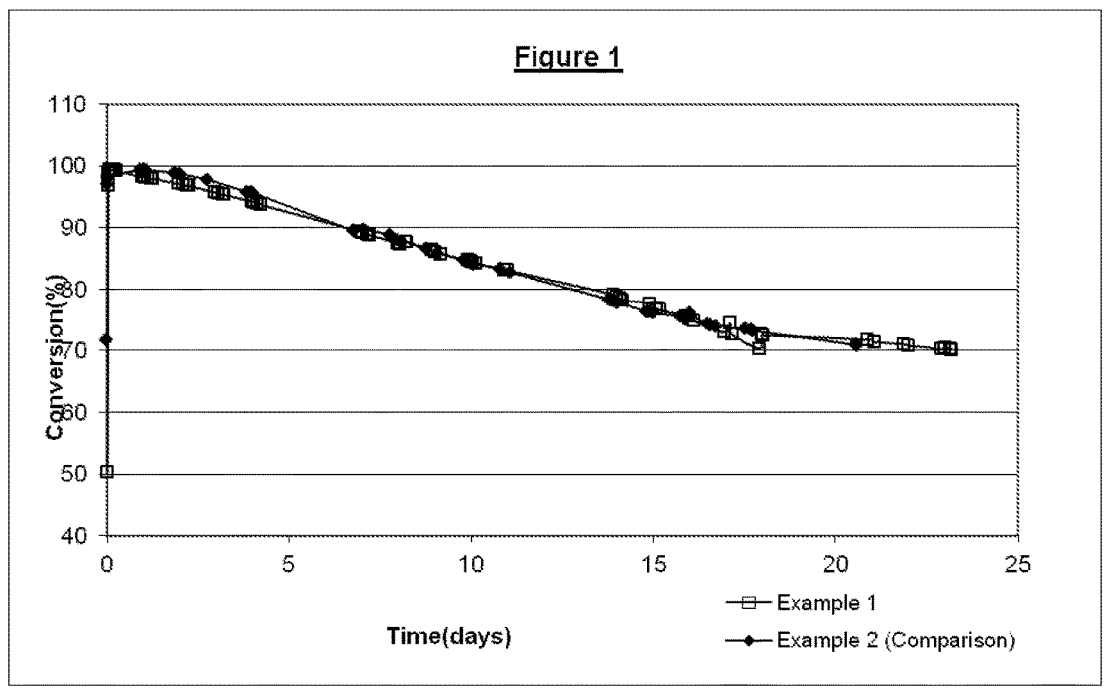
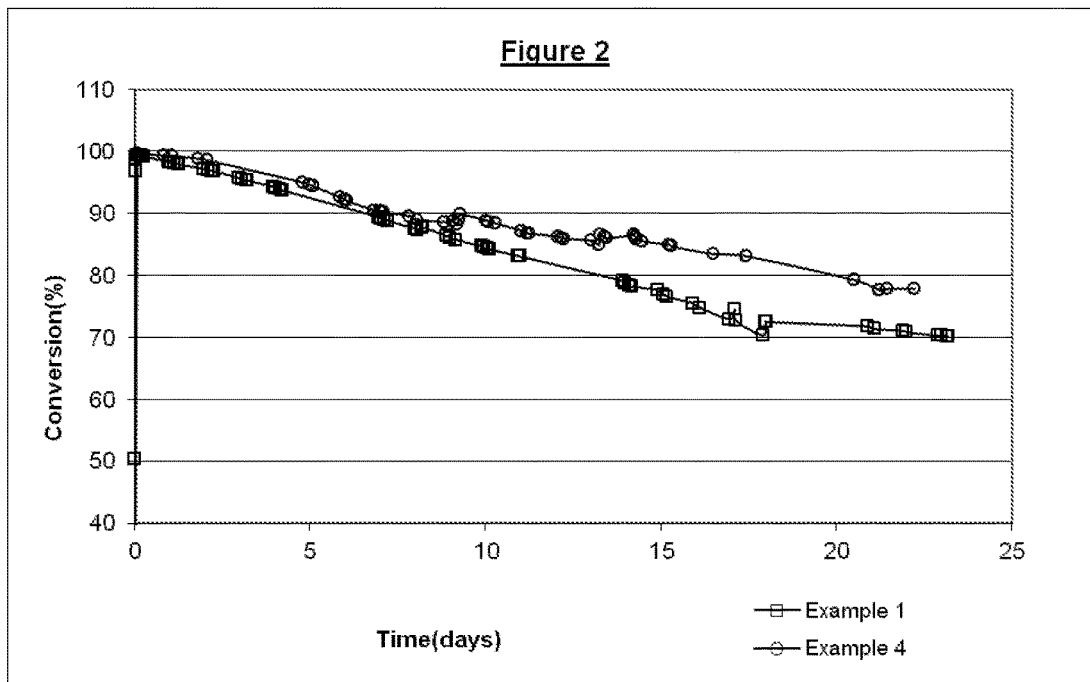

CATALYST AND METHOD FOR ITS PREPARATION

CROSS REFERENCE TO RELATED APPLICATIONS

This application is a divisional of U.S. patent application Ser. No. 14/232,294, filed on Apr. 24, 2014 (now U.S. Pat. No. 9,409,161), which is a National Stage Entry of PCT No. PCT/GB2012/051623, filed on Jul. 10, 2012, which claims the benefit of U.S. Provisional Application No. 61/510,739, filed on Jul. 22, 2011. The entire disclosures of the above applications are incorporated herein by reference.

SUMMARY OF THE INVENTION

The present invention concerns improvements in catalytic processes, and improvements in catalysts for such processes. More particularly, it concerns processes and catalysts for manufacturing vinyl chloride monomer ("VCM") from acetylene.

BACKGROUND OF THE INVENTION

One of the current state-of-the-art process for manufacturing VCM combines ethylene, hydrogen chloride and oxygen in the presence of copper chloride to form ethylene dichloride, which is decomposed at high temperature to form VCM and HCl. In an alternative process, ethyne (acetylene) from carbide is reacted with HCl over a mercury-based catalyst. This process is preferred where there is access to cheap ethyne via carbide from abundant coal resources. The mercury catalyst, usually 8-10% mercuric chloride on activated carbon, used in this process is highly toxic. Such toxicity creates problems arising from handling during manufacture of the catalyst as well as during loading of catalyst and removing catalyst after a campaign. A campaign is generally of six month duration. Deactivation of the mercury catalyst and loss of $HgCl_2$ by sublimation or volatilisation from the reactor in use can lead to significant problems. The ethyne process using a mercury-based catalyst requires a lower capital investment in plant than the ethylene process. If a non-volatile and less toxic catalyst could replace the mercury catalyst without requiring significant plant alterations in existing plant designs, this would be a significant advantage.

There have been a number of academic studies and publications which recommend a gold-based catalyst in the ethyne-HCl reaction, as being the most active catalyst for that reaction. Deactivation of gold catalysts still occurs, although it has been said that high loadings (>1 wt %) of gold on carbon reduces deactivation. Other observations on the deactivation of gold catalysts have been that deactivation occurs both at high and at low temperatures, and that low temperature deactivation appears to be caused by coke formation, probably as a result of surface reactions of vinyl chloride and ethyne.

JP 522136104 in the name of Denki Kagaku Kogyo KK, and dating from 1977, teaches the use as a catalyst in the production of VCM, of a gold halide in combination with a platinum halide or a palladium halide, on a carbon support. The preparation of the catalyst is not described, and no commercial use of the process or the catalyst appears ever to have taken place. Conte et al, (Catalysis Letters, vol. 124, no. 3-4, 22 Jul. 2008, pages 165-167), describes the reactivation of a C-supported gold catalyst when used in the hydrochlorination of acetylene. The catalyst is prepared by incipient wetness impregnation of carbon, with a solution of $HAuCl_4$ in aqua regia, followed by drying. Reactivation is by boiling in aqua regia. BonganiNkosiet al, (Journal Of Catalysis, Vol. 128, 1991, pages 378-386) describes hydrochlorination of acetylene using C-supported gold catalysts made by incipient wetness impregnation of an extruded carbon with a solution of $HAuCl_4$ in aqua regia and reactivation with HCl in situ. Thompson (Gold Bulletin, vol. 31, no. 4, 1998, pages 111-118) discusses hydrochlorination of ethyne using gold catalysts made by impregnation of activated carbon with chloroauric acid dissolved in aqua regia.

There remains a need for a catalysed process for the production of VCM from ethyne that can be used in new or in existing plants using a catalyst which resists deactivation or at least has no worse lifetime, and has desirably a longer effective life, than the mercury catalyst, and which uses a catalyst that has little or no toxicity. WO2010/055341 describes a catalyst comprising gold nanoparticles carried on a carbon support which is active for the reaction of ethyne with hydrogen chloride to form vinyl chloride. The catalyst is made by impregnating an extruded carbon support with a solution of $HAuCl_4$ in aqua regia, which is a concentrated mixture of hydrochloric and nitric acids. Use of aqua regia adds complexity to the manufacturing process because it is toxic and also highly oxidising, so that the manufacturing equipment must be protected from damage by the acid. Also the removal of excess acid results in the creation of HCl and NOx vapours which must be treated to avoid environmental pollution and to maintain a safe working environment. We have now found an improved catalyst and method for its manufacture which does not employ aqua regia as a process solution and which therefore avoids some of the problems associated with making the catalysts of the prior art.

SUMMARY OF THE INVENTION

According to the invention we provide a method of manufacturing a catalyst comprising gold on a support, comprising the steps of impregnating said support with a solution of gold or a compound thereof and a sulphur-containing ligand to form a gold complex and then drying the impregnated support.

According to a second aspect of the invention, we provide a catalyst comprising a complex of gold with a sulphur-containing ligand on a support.

An alternative catalyst according to the invention comprises gold, or a compound thereof, and trichloroisocyanuric acid or a metal dichloroisocyanurate on a support. A method of manufacturing this alternative catalyst comprises the steps of impregnating said support with a solution of gold or a compound thereof and a solution of at least one of trichloroisocyanuric acid or a metal dichloroisocyanurate and then drying the impregnated support.

According to the invention, we further provide a chemical process comprising reacting at least one chemical substrate in the presence of a catalyst comprising gold or a compound of gold and either
a) sulphur,
b) a compound of sulphur, or
c) trichloroisocyanuric acid or a metal dichloroisocyanurate on a support. Preferred processes include processes for the oxidation of a chemical substrate, and a process for the hydrochlorination of an alkyne comprising reacting said alkyne with HCl in the presence of the catalyst. Preferably the catalyst comprises a complex of gold with a sulphur-containing ligand.

DETAILED DESCRIPTION OF THE INVENTION

In the catalyst of the invention, the active catalytic species comprises gold in a positive oxidation state, such as $Au^{3+}$ and $Au^{1+}$, although some of the gold present may be in the form of metallic gold ($Au^0$). In some embodiments of the invention, the catalysts may be considered to comprise gold particles having a core comprising metallic gold and a shell or surface layer comprising higher oxidation state gold species including $Au^{3+}$. The shell need not be complete, but preferably all or substantially all the exposed surface of the particle has the surface higher oxidation state gold species; for example if the metallic gold is partially surrounded by support, the "shell" may extend only over the exposed particle surface. $Au^{3+}$ need not be the only higher oxidation state gold species present in the shell, and $Au^{1+}$ may also be present, for example. Such higher oxidation state species may be stabilised by halide, for example in prior art catalysts. It has been widely proposed in the prior art that the higher oxidation state gold species are the active species for catalysing the reaction of acetylene with HCl. We postulate that, in the catalysts of the invention, the gold is stabilised in a higher oxidation state by complexation with sulphur-containing ligands or highly oxidising chlorine-providing species. This prevents rapid reduction of the gold complex to bulk metallic gold by the carbon of the support, the latter effect leading to poor gold dispersion and poor catalytic activity. The core of the particles typically comprises metallic gold($Au^0$) but other gold species may also be present in the core. Without wishing to be bound by any theory, it is considered likely that the metallic gold in the core and the $Au^{3+}$ and/or other positive oxidation state species in the shell act as a redox couple, or the metallic gold core acts as an electron sink during hydrochlorination reaction(s).

The amount of gold in the catalyst depends on the proposed process for which it is made. Typically the catalyst contains from 0.01-10% of gold, by weight of the total catalyst, especially 0.05-5%, for example <1% such as 0.05-0.8%. For use in the hydrochlorination of acetylene, we prefer a catalyst containing 0.05-1%, especially 0.05-0.6% of gold, by weight. In some applications, catalysts containing 0.1%-1% of gold, e.g. 0.1-0.6%, may be very useful.

It is surprising that the presence of sulphur has been found to be advantageous in the catalyst of the present invention. Sulphur is known to be a catalyst poison in many reactions and its deliberate incorporation into a precious metal catalyst would not normally be considered.

Any known catalyst support may be used to make the catalyst of the invention. Typical metal oxide supports such as alumina, silica, zeolite, silica-alumina, titania or zirconia and composites thereof may be used. Catalyst supports made from carbon are also suitable for use in the present invention, including carbon from natural sources (peat, wood, coal graphitic, etc or combinations thereof) or synthetic carbons. The carbon is preferably an activated carbon, activated for example by steam, acid, or otherwise chemically activated. Preferred carbon supports include a high surface area activated carbon, preferably of surface area greater than 800 $m^2/g$, such as a 1300 $m^2/g$ carbon extrudate. Carbon extrudates are available as "high purity" or "ultra-high purity" grades commercially and such grades are typically acid washed to remove impurities. A combination of metal oxide and carbon may also be used as a catalyst support. The catalyst support may take the form of powders, granulates or particles formed in various shapes, ("shaped units") such as spheres, tablets, cylinders, multi-lobed cylinders, rings, miniliths etc. or a massive catalyst unit such as a monolith. Alternatively the catalyst in the form of a powder may be included in a coating formulation and coated onto a reactor wall or shaped substrate such as a monolith. One preferred form of catalyst support comprises a plurality of shaped units in the form of cylinders, spheres or lobed cylinders each having a diameter of 1-10 mm, or, more preferably a diameter in the range 3-5 mm. In the case of a cross-section shape having a non-uniform diameter, such as a lobed cylinder, the diameter is an average diameter. Such catalyst support shapes are commercially available and may be made by extrusion, tabletting or by other methods.

The sulphur may be present in the catalyst as elemental sulphur or, more preferably, in the form of a sulphur compound containing sulphur in a reduced or oxidised state or a combination of reduced and oxidised states, for example as in the thiosulphate ion. The sulphur may be present in the form of a sulphur compound which is not a ligand complexed to the gold. Preferably, however, the sulphur is present in a sulphur-containing compound which is a ligand capable of forming a complex with a gold species or which is complexed with the gold species. More preferably, the sulphur-containing ligand is capable of stabilising gold in a positive oxidation state. Suitable sulphur-containing ligands are oxidising ligands, especially oxygen donating ligands, containing sulphur in a positive oxidation state, or sulphur-donating ligands. Without wishing to be bound by theory, we believe such ligands to be effective in stabilising the $Au^{3+}$ and or $Au^+$ species, leading to improved catalysts. Preferred sulphur-containing compounds include sulphates, sulphonates, thiosulphates, thiocyanates, thiourea, thionyl chloride, thiopropionic acid and thiomalic acid.

The amount of sulphur in a fresh catalyst is preferably in the range from about 0.005-15% by weight, more preferably from 0.03 to 7% by weight in the dry catalyst, especially up to about 5% by weight. In one embodiment of the invention, in which the gold complex is a gold-thiosulphate complex, the mole ratio of S to Au in the complex is preferably in the range from about 3:1 to about 8:1. In such an embodiment containing a preferred amount of gold, the amount of sulphur in the catalyst may be in the range of 0.03 to 1.50% by weight. Some sulphur originating from sources other than the S-containing complex may also be present in the catalyst, for example incorporated in the support material. The amount of sulphur present in the catalyst may decrease during use in a process. For example, in a process for the hydrochlorination of alkynes, we postulate that when the catalyst reacts with HCl, either in a pre-activation step or during the reaction with alkyne, the chloride forms a mixed complex of gold with the sulphur species. The sulphur appears to be lost over time in the process, possibly by formation of sulphur-oxygen compounds. It is possible that a gold catalyst may be at least partially reactivated, following use in a process by treatment with a sulphur-containing compound. Other reactivation procedures using a halide such as HCl or an alkyl halide such as methyl iodide are known and may be useful in a process using the catalysts of the invention.

The catalyst may additionally comprise a metal other than gold or any metal forming the support compound. Known promoters for use with gold catalysts used for hydrochlorination reactions include compounds of cobalt, copper or lanthanum and such metals may be present in the catalysts of the invention or the catalysts used in the process of the invention. We have found that Group 1 and Group 2 metals may also be advantageously incorporated in the catalysts of the invention. Therefore the catalyst may comprise, in addition to gold, a metal or a compound of a metal selected from the group consisting of cobalt, copper, lanthanum, cerium, lithium, sodium, potassium, rubidium, caesium, magnesium, calcium, strontium and barium. The additional metal may be present as a promoter or may have another function in the catalyst or its preparation. For example, some metals, such as calcium, are believed to inhibit the formation of carbon deposits on the catalysts and can therefore be used to help maintain the activity of the catalyst over a period of time. Therefore, even if the presence of a metal does not increase the activity of a catalyst in the short-term it may be regarded as a promoter if it reduces the tendency of a catalyst to deactivate during its use in a reaction or has another beneficial effect on the practical use of the catalyst.

Catalysts may be prepared using a variety of catalyst preparation techniques known generally in the art, for example impregnation, preferably using incipient wetness methods, deposition, precipitation and combinations of these. In the method of manufacturing a catalyst according to the invention the catalyst is preferably made by impregnating the support with a solution of a complex of gold with a sulphur-containing ligand. Preferred complexes are therefore soluble in readily available solvents which present few environmental hazards. A preferred solvent is water. Preferred solutions for impregnation include aqueous solutions of gold sulphates, sulphonates, thiosulphates, thiocyanates, thiourea, thionyl chloride, thiopropionic acid and thiomalic acid. In one preferred embodiment the method of the invention comprises impregnating a particulate carbon support with an aqueous solution containing a compound of gold and a compound containing a thiosulphate ion, followed, if necessary, by separation of excess solution and then drying the impregnated material. It is preferred that the impregnation is carried out by the incipient wetness or "pore-filling" protocol, in which the amount of solution used is calculated to be just fill the pores of the support. We believe that the compound of gold and compound containing a thiosulphate ion together form a gold-thiosulphate complex. Typically, using an incipient wetness method of impregnation, the volume of solution used is 100%± up to about 20% of the measured (or calculated) pore volume of the support. The support is usually mixed with the solution by tumbling or the solution may be added, e.g. drop-wise or by spraying, to an agitated bed of support over a period of time. As an alternative, the catalyst support may be impregnated with the solution containing the gold compound and/or the sulphur-containing compound or trichloroisocyanurate using an excess volume of solution so that the gold, sulphur-compound and/or trichloroisocyanurate is deposited on the catalyst support by absorption or by ion-exchange reactions. As a further alternative, deposition-precipitation methods may be used. The person skilled in the art of catalyst manufacture is acquainted with such methods of preparing catalysts by impregnation of support materials with a solution of active metal compounds.

The amount of the gold and sulphur compounds in the impregnating solution is calculated to provide the required amount of gold and sulphur in the finished catalyst. The gold is normally present in the catalyst as a layer. Typically, in a 3 mm catalyst particle for example, the gold is present in a layer of up to about 300 microns thick, extending inwardly from the surface of the catalyst support. However the gold may be uniformly distributed throughout the catalyst particle.

The catalyst may be made by adding the sulphur-containing compound and a gold-containing compound separately to a catalyst support. For example, a support may be treated with a sulphur-containing compound, optionally dried or heated and then treated with a gold compound, e.g. by impregnation, so that a higher oxidation state gold complex may be formed in situ upon addition of the gold compound. Alternatively a material comprising a catalyst support and a gold compound supported thereon may be treated with a sulphur-containing compound. As a further alternative, a catalyst support comprising a sulphur-containing material may be used to form the catalyst. Methods of treatment with sulphur-containing compounds especially sulphides, e.g. hydrogen sulphide, to deposit sulphur on the catalyst may be used.

The impregnation solution containing the gold compound may contain an additional metal compound, for example including a compound of a metal selected from the group consisting of cobalt, copper, lanthanum, cerium, lithium, sodium, potassium, rubidium, caesium, magnesium, calcium, strontium and barium. The additional metal, if present, may alternatively be added to the catalyst in a separate step, for example by impregnating a gold-containing catalyst particle with a solution of a compound of the additional metal, or by impregnating a support material with such a solution before the gold compound is added to the catalyst.

When a carbon support is used, an acid wash, preferably using hydrochloric acid, nitric acid, phosphoric acid or sulphuric acid, may be carried out prior to impregnation with the gold compound. This may be done, for example, by dispersing the carbon in hydrochloric acid, optionally heating, possibly to boiling, draining, washing with distilled or deionised water and drying in air. As an alternative to using an acid wash procedure in the preparation of the catalyst a pre-treated or acid washed support may be obtained from a manufacturer of carbon supports as a commercial material when it is desired to use an acid-washed form of carbon support.

The catalyst may require an activation step prior to use in a chemical process. In such cases it may be more correct to refer to the dried, impregnated catalyst support as a catalyst precursor, but, for simplicity, we refer to such materials as catalysts, whether or not they require activation (or pre-activation) to attain their full catalytic activity.

A preferred chemical process of the invention comprises a process for the manufacture of vinyl chloride by hydrochlorination of acetylene, comprising reacting acetylene with HCl in the presence of a catalyst comprising gold and sulphur on a support. Preferably the catalyst is a catalyst according to the invention and/or made using a method of the invention. The process is carried out at elevated temperature, usually between about 150° C. and 250° C., more preferably <200° C. The HCl and acetylene are preferably premixed and also preferably pre-heated to the reaction temperature. Normally HCl is present in excess of the amount required for the stoichiometric reaction. The catalyst may be present in the reactor in the form of a fixed bed of catalyst particles arranged such that the feed gases are passed over or through the catalyst bed. Alternative reactor arrangements may be used, including fluidised beds or other moving bed arrangements. The catalyst may alternatively be provided in the form of a monolith or coated on the wall of a reactor vessel. The catalyst bed may be provided with means to regulate the temperature in order to avoid overheating due to the exothermic reaction or to raise the temperature if required. It is preferred to treat the catalyst with HCl before use in the process. This treatment is typically carried out by flowing HCl over the catalyst for a period of at least an hour at a temperature of at least 50° C., especially >100° C. This pre-treatment may take place in the reactor by operating with a flow of HCl without the acetylene, at a suitable temperature.

BRIEF DESCRIPTION OF THE DRAWINGS

The invention will now be further described in the following examples with reference to the attached drawings.

FIG. 1: Plot of conversion vs time for catalysts of Examples 1 and 2

FIG. 2: Plot of conversion vs time for catalyst of Examples 1 and 4

EXAMPLES

Example 1

Preparation of Catalyst According to the Invention

A sufficient quantity of 3 mm steam activated carbon extrudates was crushed, and then sieved, to yield 52 g of particles with diameters between 0.7 mm and 1.4 mm. This material was soaked in a solution of HCl, made by dilution of 60 ml 36% HCl with 240 ml demineralised water, for 20 minutes and then washed twice with 300 ml demineralised water per wash. Thereafter the material was dried at 105° C.

Ammonium thiosulphate (0.460 g) was dissolved in 42 ml water. A solution of $HAuCl_4$ containing 0.143 g Au was added slowly to this solution with stirring to give a deep yellow-brown solution. 47.3 g of the sieved and acid-washed carbon was then impregnated with the gold thiosulphate solution described above using an incipient wetness technique. After standing for 30 minutes the material was dried overnight at 120° C. The resulting catalyst contained 0.34% Au, by weight. Analysis of the samples to determine the concentration of metals was carried out by ICP-OES (inductively coupled plasma-optical emission spectroscopy) following microwave digestion of the samples.

Example 2

(Comparative) Preparation of a Prior Art Catalyst

An aqua-regia solution was prepared by mixing 5.8 ml $HNO_3$ (69%) with 19.3 ml HCl (36%) and 3.9 ml of demineralised water. A solution of $HAuCl_4$ containing 0.336 g Au was added to the aqua regia solution. 35 g of crushed and sieved carbon extrudates, (sieved to a particle size range of 0.7-1.4 mm) were impregnated with the gold-aqua regia solution using an incipient wetness technique. After standing for about 16 hours, the material was dried at 140° C. for 7 hours. The resulting catalyst contained 0.75% Au, by weight.

Example 3

Test for Activity Over Time in Hydrochlorination of Acetylene.

12.0 g of a catalyst as described in Example 1 (or Example 2) was loaded into a 7 mm diameter stainless steel tube, coiled so as to form a spiral shape, giving a bed length of 1 metre. Initially the sample was dried at 120° C. under a stream of dry nitrogen. The reactor was then heated to 180° C., and a flow of the mixed reactant gases was initiated (85 ml/min acetylene, 102 ml/min hydrogen chloride). Initially nearly 100% conversion was achieved, which slowly decreased to about 70% over the course of 24 days. The results (shown in FIG. 1) show that the activity of the 0.3% Au thiosulphate catalyst of Example 1 is comparable with the catalyst made in Example 2 from an aqua regia solution, having a much higher gold content (0.75%).

Example 4

Activity of Pre-Chlorinated Catalyst 12.0 g of a catalyst made as described in Example 1 was loaded into a 7 mm diameter stainless steel tube reactor, as described in Example 3. Initially the sample was dried at 120° C. under a stream of dry nitrogen. The reactor was then heated to 180° C., and a stream of hydrogen chloride (102 ml/min) was passed through the reactor for 4 hours to activate the catalyst. Acetylene was then introduced to give a mixed gas flow of 85 ml/min acetylene, 102 ml/min hydrogen chloride. The results (FIG. 2) show that the HCl pre-activation produces a significant increase in conversion compared with the non-activated sample during the course of the run.

Example 5

Preparation of Catalyst According to the Invention 5.8 g of 3 mm steam-activated carbon extrudates were soaked in 100 ml of 2M HCl for 30 minutes. The carbon was then washed with 2×50 ml portions of deionised water and dried at 120° C.

Ammonium thiosulphate (0.186 g) was dissolved in 4.8 ml water. A solution of $HAuCl_4$ containing 0.06 g of gold was added slowly to this solution with stirring to give a deep yellow-brown solution. The acid-washed carbon was then impregnated with this solution using the incipient wetness technique. The product was dried at overnight at 120° C. The resulting catalyst contained 1.0% Au, by weight.

Analysis of the resulting catalyst particles by electron probe microanalysis (EPMA) showed that the particles had a gold layer around their periphery to a thickness of about 200 microns Example 6

(Comparative) Preparation of Prior-Art Catalyst.

58 g of carbon extrudates were impregnated with an aqua-regia solution of gold chloride prepared by mixing 9.5 ml $HNO_3$ (69%) with 32 ml HCl (36%) and 6.5 ml of demineralised water and a solution of $HAuCl_4$ containing 0.58 g Au. After standing for about 16 hours, the material was dried at 140° C. for 7 hours. Inspection of the resulting catalyst particles by EPMA showed that the particles had a gold layer around their periphery to a thickness of about 200 microns.

Example 7

(Comparative) Preparation of Catalyst from Aqueous Gold Chloride

A gold solution was prepared by mixing 0.14 g of $HAuCl_4$ aqueous solution containing 41% Au with 4.8 ml of water. 6 g of 3 mm carbon extrudates were impregnated with this solution to incipient wetness. After standing the material was dried overnight at 105° C. The particles contained 1% gold, by weight. EPMA showed a gold layer having a thickness of 10 microns. This result indicates that the gold(III) ions are reduced to metallic gold when they contact the carbon of the support, which is a reducing material. The gold is therefore poorly dispersed and predominantly in a less active state than in the catalysts of the invention.

Example 8

Test for Activity at 24 Hours 1.5 g of catalyst was loaded into a 4 mm diameter glass reactor, giving a bed depth of 30 cm. Initially the sample was dried at 110° C. under a stream of dry nitrogen. The reactor was then maintained at 110° C., and a flow of the mixed reactant gases was initiated, diluted with nitrogen (50 ml/min acetylene, 60 ml/min hydrogen chloride, 120 ml/min nitrogen). These conditions are selected to give a maximum conversion for the catalysts of about 50% in order that different catalysts can be compared.

The catalysts typically take up to 24 hours for the conversion behaviour to stabilise, thereafter following a more gradual and predictable decline. The conversion value after 24 hours, used as a measure of the relative activity of the catalyst, is shown in Table 1.

Examples 9-16

Catalysts were prepared by impregnation of the carbon support with a solution of a gold compound/complexing agent, using the incipient wetness method as generally described in Examples 5-7. The amount of gold in the solution was calculated to provide a finished catalyst containing 1% of gold by weight. The gold compound, complexing agent and the solvent used are listed in Table 1. Example 9 was made without using any gold compound, i.e. as a blank for comparison. The catalysts were tested using the procedure described in Example 8 and the results, in the form of conversion % after 24 hours, are shown in Table 1.

TABLE 1

| Catalyst | Gold precursor compound | solvent | % Conversion at 24 hours |
| --- | --- | --- | --- |
| Example 5 | $HAuCl_4$ + $(NH_4)_2S_2O_3$ | water | 23 |
| Example 6 (Comparative) | $HAuCl_4$ + aqua regia | aqua regia | 22 |
| Example 7 (Comparative) | $HAuCl_4$ | water | 5 |
| Example 9 (Comparative) | none | aqua regia | 3 |
| Example 10 | $HAuCl_4$ + $(Na)_2S_2O_3$ | water | 27 |
| Example 11 | $HAuCl_4$ + $CaS_2O_3$ | water | 23 |
| Example 12 | $HAuCl_4$ + trichloroisocyanuric acid | methanol | 22 |
| Example 13 | $HAuCl_4$ + sodium dichloroisocyanurate | water | 20 |
| Example 14 | $HAuCl_4$ + potassium dichloroisocyanurate | water | 13 |
| Example 15 | sodium gold thiosulphate | water | 13 |
| Example 16 | $HAuCl_4$ + thiomalic acid | water | 10 |

Example 17

Preparation of Catalyst According to the Invention 3 mm diameter carbon extrudates (2065 g) were soaked in hydrochloric acid, prepared by dilution of 0.75 l 36% HCl with 2.90 l demineralised water, for 1.5 hour and thereafter washed with demineralised water and dried at 110° C. overnight. A solution of $HAuCl_4$ containing 11.00 g Au was diluted in 270 ml demineralised water. 35.66 g ammonium thiosulphate was dissolved in 1.0 l demineralised water. A gold thiosulphate solution was prepared by addition of the $HAuCl_4$ solution to the ammonium thiosulphate solution with stirring. 1810 g of the same carbon extrudates were then impregnated with the gold thiosulphate solution using an incipient wetness technique. After standing the material was dried overnight at 125° C. The resulting catalyst contained 0.66% Au by weight.

Example 18

Preparation of Catalyst According to the Invention 3 mm diameter carbon extrudates (7100 g) were soaked in hydrochloric acid, prepared by dilution of 2.575 l 36% HCl with 10.000 l demineralised water, for 1 hour and thereafter washed with demineralised water and dried at 125° C. overnight.

A solution of $HAuCl_4$ containing 21.10 g Au was diluted in 1.35 l demineralised water. 68.46 g ammonium thiosulphate was dissolved in 3.5 l demineralised water. A gold thiosulphate solution was prepared by addition of the $HAuCl_4$ solution to the ammonium thiosulphate solution with stirring and diluted to a final solution volume of 4875 ml. 6950 g of the carbon extrudates were then impregnated with the gold thiosulphate solution using an incipient wetness technique. After standing the material was dried overnight at 125° C. The resulting catalyst contained 0.37% Au by weight.

Example 19

Catalysts according to the invention were tested using the procedure described in Example 8 and the results, in the form of conversion % after 24 hours, are shown in Table 2.

TABLE 2

| Catalyst | % Au in catalyst | % Conversion at 24 hours |
| --- | --- | --- |
| Example 5 | 1.00 | 23 |
| Example 17 | 0.66 | 26 |
| Example 18 | 0.37 | 15 |

Example 20

A solution of $HAuCl4$ containing 2.71 g Au was diluted in 470 ml demineralised water and added to a solution of 8.78 g ammonium thiosulphate dissolved in 470 ml demineralised water. Thereafter the solution was diluted to a final volume of 950 ml. Carbon extrudates (3 mm diameter, acid washed, steam activated carbon) were used as received from commercial suppliers. 1888 g of the carbon extrudates were impregnated with the gold containing impregnation solution using an incipient wetness technique. After standing, the material was dried overnight at 120° C. ICP-OES analysis of the material produced indicated an Au assay of % Au=0.130% by weight.

The catalyst was tested as described in Example 8 and the conversion after 24 hours was found to be 11.6%.

Example 21

Preparation and Testing of Catalyst Including Co

A different sample of a catalyst was prepared substantially as described in Example 18, and tested according to the procedure described in Example 8. After 24 hours, a conversion of 19% was measured. 5.8 g of the same fresh catalyst was impregnated with 4.8 ml of an aqueous solution of the cobalt complex [Co(NH$_3$)$_4$]Cl$_3$, the concentration of Co being such as to give a 3:1 Co:Au molar ratio. After drying overnight at 125° C., the resulting Co-doped catalyst was tested as described in Example 8. After 24 hours, a conversion of about 33% was measured, showing a substantial enhancement over the original catalyst.

Example 22

A solution of HAuCl$_4$ containing 0.972 g Au was diluted in 100 ml demineralised water and added to a solution containing ammonium thiosulphate (3.0 g) in 100 ml demineralised water. The resultant solution was further diluted with demineralised water to a final volume of 375 ml. 4 mm diameter commercially supplied carbon extrudates (acid washed, steam activated carbon) were used as received. 635 g of the carbon extrudates were impregnated with the gold containing impregnation solution using an incipient wetness technique. After standing, the material was dried overnight at 105° C.

ICP-OES analysis of the material produced indicated an Au assay of Au=0.130% by weight.

Example 23

Preparation of Catalyst Including Ca 0.174 g of Ca(OH)$_2$ was dissolved/slurried in 50 ml demineralised water and added to a solution of HAuCl$_4$ containing 0.927 g Au in 50 ml demineralised water to form a solution of Ca(AuCl$_4$)$_2$. Ammonium thiosulphate (3.0 g) was dissolved in 50 ml demineralised water and added to the solution of Ca(AuCl$_4$)$_2$. The resultant impregnation solution was diluted to a final volume of 375 ml. 635 g of 4 mm diameter commercially supplied carbon extrudates (acid washed, steam activated carbon) were impregnated with the gold containing impregnation solution using an incipient wetness technique. After standing, the material was dried overnight at 105° C. ICP-OES analysis of the dried material indicated assays of Au=0.125%, Ca=0.04% by weight.

Example 24

Alternative Preparation of Catalyst Including Ca

A solution of HAuCl$_4$ containing 0.927 g Au in 100 ml demineralised water was added to a solution containing ammonium thiosulphate (3.0 g) and CaCl$_2$ (0.5 g) in 100 ml demineralised water. The resultant solution was further diluted with demineralised water to a final volume of 375 ml. 635 g of the 4 mm diameter carbon extrudates (acid washed, steam activated carbon) were impregnated with the gold-containing impregnation solution using an incipient wetness technique. After standing, the material was dried overnight at 105° C. ICP-OES analysis of the material produced indicated assays of Au=0.130%, Ca=0.05% by weight.

Example 25

Catalyst Testing

Catalysts prepared as described in Examples 22-24 were tested using the following method. 4.36 g of catalyst, in the form of 4 mm extrudates, was loaded into a 40 mm diameter glass reactor, giving a bed depth of 20 cm. Initially the sample was dried at 120° C. under a stream of dry nitrogen. The reactor was then maintained at 120° C., the nitrogen flow stopped, and a flow of the mixed reactant gases was initiated (28.5 ml/min acetylene, 34.2 ml/min hydrogen chloride). The flow of the reactant gases was then increased in steps over a 45 minute period, reaching the maximum flow of 114 ml/min acetylene, 125 ml/min hydrogen chloride, which was maintained over the duration of the experiment. Whilst the external temperature was maintained at 120° C., the internal bed temperature was monitored to ensure that the temperature did not exceed 180° C. as the gas flow was increased. These conditions are selected so as to minimise thermal deactivation caused by the exothermic reaction of acetylene with hydrogen chloride.

The catalysts typically take up to 24 hours for the conversion behaviour to stabilise, thereafter following a more gradual and predictable decline. The conversion value after 24 hours, used as a measure of the relative activity of the catalyst, is shown in Table 3.

TABLE 3

| Catalyst | % Au in catalyst | Other metal present (% by weight) | % Conversion at 24 hours |
| --- | --- | --- | --- |
| Example 22 | 0.130 | none | 55 |
| Example 23 | 0.125 | Ca (0.04) | 49 |
| Example 24 | 0.130 | Ca (0.05) | 49 |

The invention claimed is:

1. A catalyst comprising gold, or a compound thereof, and trichloroisocyanuric acid or a metal dichloroisocyanurate on a support.

2. The catalyst according to claim 1, comprising from 0.01-10% of gold, by weight based on the weight of the total catalyst.

3. The catalyst according claim 1, wherein said support comprises carbon.

4. The catalyst according to claim 1, wherein said support comprises a metal oxide.

5. The catalyst according to claim 1, wherein said support is in the form of a powder, granulate or shaped unit.

6. The catalyst according to claim 1, wherein at least some of the gold is in a positive oxidation state.

7. The catalyst according to claim 1, further comprising a metal or a compound of a metal selected from the group consisting of cobalt, copper, lanthanum, cerium, lithium, sodium, potassium, rubidium, caesium, magnesium, calcium, strontium and barium.

8. A method of manufacturing the catalyst of claim 1, comprising the steps of:
impregnating a catalyst support with a solution of gold or a compound thereof and a solution of at least one of trichloroisocyanuric acid or a metal dichloroisocyanurate; and
drying the impregnated catalyst support.

9. A chemical process comprising reacting at least one chemical substrate in the presence of a catalyst comprising:
a) gold, or a compound thereof; and
b) trichloroisocyanuric acid or a metal dichloroisocyanurate, on a support.

10. The chemical process according to claim 9, comprising oxidation of said chemical substrate.

11. The process according to claim 9, wherein the chemical process is hydrochlorination of an alkyne comprising reacting said alkyne with hydrogen chloride in the presence of said catalyst.

12. The process according to claim 11, wherein the catalyst comprises from 0.01-10% by weight of gold.

13. The process according to claim 12, wherein the catalyst comprises from 0.01-0.6% by weight of gold.

14. The process according to claim 11, further comprising a step of treating said catalyst with hydrogen chloride in the absence of acetylene.

15. The process according to claim 11, wherein said support comprises carbon.

16. The process according to claim 11, wherein said support comprises a metal oxide.

17. The process according to claim 11, wherein said support is in the form of a powder, granulate or shaped unit.

18. The process according to claim 11, wherein at least some of the gold is in a positive oxidation state.

19. The process according to claim 11, wherein said catalyst further comprises a metal or a compound of a metal selected from the group consisting of cobalt, copper, lanthanum, cerium, lithium, sodium, potassium, rubidium, caesium, magnesium, calcium, strontium and barium.

* * * * *